(12) United States Patent
Ueno (10) Patent No.: US 11,581,172 B2
(45) Date of Patent: Feb. 14, 2023

(54) METHOD FOR MASS SPECTROMETRY AND MASS SPECTROMETER

(71) Applicant: SHIMADZU CORPORATION, Kyoto (JP)

(72) Inventor: Yoshihiro Ueno, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 8 days.

(21) Appl. No.: 17/474,617

(22) Filed: Sep. 14, 2021

(65) Prior Publication Data

US 2022/0172938 A1   Jun. 2, 2022

(30) Foreign Application Priority Data

Nov. 27, 2020   (JP) .............................. JP2020-196605
Aug. 4, 2021   (JP) .............................. JP2021-128382

(51) Int. Cl.
*H01J 49/00*   (2006.01)
*H01J 49/16*   (2006.01)
*G01N 33/00*   (2006.01)
*G01N 27/64*   (2006.01)

(52) U.S. Cl.
CPC .......... *H01J 49/0031* (2013.01); *G01N 27/64* (2013.01); *G01N 33/0027* (2013.01); *H01J 49/16* (2013.01)

(58) Field of Classification Search
CPC .... G01N 30/02; G01N 30/06; G01N 33/0027; H01J 49/14; H01J 49/16; H01J 49/0031; H01J 49/147
See application file for complete search history.

(56) References Cited

U.S. PATENT DOCUMENTS

2016/0247669 A1*   8/2016   Tateishi ................ H01J 49/067

FOREIGN PATENT DOCUMENTS

JP          2016-157523 A       9/2016

* cited by examiner

*Primary Examiner* — David E Smith
*Assistant Examiner* — Hsien C Tsai
(74) *Attorney, Agent, or Firm* — Sughrue Mion, PLLC (57) ABSTRACT

In order to suppress a charge-up in an ion source configured to ionize a component contained in a sample gas, a mass spectrometer according to the present invention is provided with an ion source (3) including: an ionization chamber (30) having an ion ejection opening (301) and internally having a space substantially separated from an outside area; a repeller electrode (31), located within the ionization chamber, for creating an expelling electric field which acts on an ion generated within the ionization chamber to expel the ion through the ion ejection opening to the outside area; and a voltage generator (7) configured to selectively apply, to the repeller electrode, a first voltage for creating the expelling electric field and a second voltage for creating a charge-up-removing electric field, where the second voltage is a positive voltage having a larger absolute value than the first voltage.

7 Claims, 6 Drawing Sheets

METHOD FOR MASS SPECTROMETRY AND MASS SPECTROMETER

TECHNICAL FIELD

The present invention relates to a method for mass spectrometry and a mass spectrometer, and more specifically, to a method for mass spectrometry and a mass spectrometer using an ion source which employs an electron ionization (EI) method, chemical ionization (CI) method or negative chemical ionization (NCI) method.

BACKGROUND ART

In a mass spectrometer included in a gas chromatograph mass spectrometer (GC-MS), an EI, CI or NCI method (or other ionization methods) is mainly used for ionizing a compound in a sample gas. In this type of mass spectrometer, the compound in a sample gas introduced into an ionization chamber is ionized by an appropriate ionization method mentioned earlier. The generated ions are transported through an ion transport optical system to a mass separator, such as a quadrupole mass filter. In the mass separator, the ions are separated from each other according to their mass-to-charge ratios (strictly speaking, this should be written as "m/z" in italic type, although the term "mass-to-charge ratio" is used in this description according to common practices) and detected.

Figure 6:
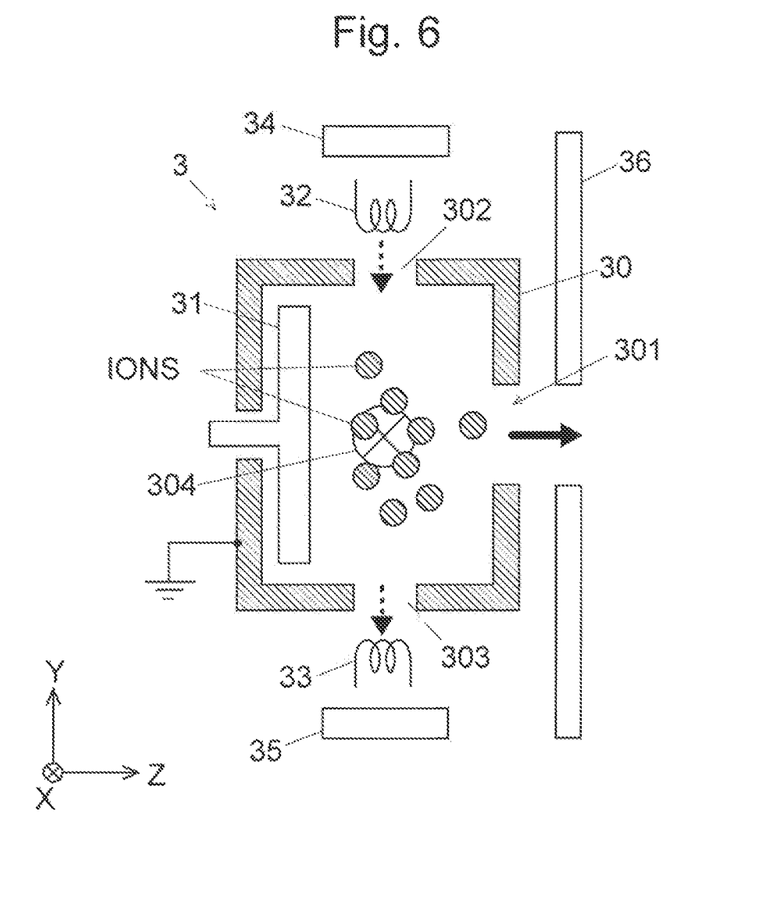
FIG. 6 is a schematic configuration diagram of a common EI ion source.

FIG. 6 is a schematic configuration diagram of a common EI ion source disclosed in Patent Literature 1 (or other related documents). For convenience of explanation, the three axes of X, Y and Z orthogonal to each other are defined within the space.

This ion source 3 includes a box-shaped ionization chamber made of an electrically conductive material. A repeller electrode 31 is located within the ionization chamber 30. An electron-introducing hole 302 is formed in the upper wall of the ionization chamber 30, while an electron discharge opening 303 is formed in the lower wall. A filament 32 is located on the outside of the electron introduction opening 302, while a trap electrode (which is actually a filament) 33 is located on the outside of the electron discharge opening 303. A pair of magnets 34 and 35 are located on the outsides of the filament 32 and the trap electrode 33, respectively, so as to face each other, with the filament 32 and the trap electrode 33 in between. An ion ejection opening 301 is formed in the front wall of the ionization chamber 30 (which is opposite to the wall at which the repeller electrode 31 is located), and an extraction electrode 36 is located on the outside of this opening 301. A sample-gas introduction tube 304 is connected to a side wall of the ionization chamber 30. In this example, the ionization chamber 30 is grounded and has a potential of 0 V.

During an analysis, an electric current is supplied from a power source (not shown) to the filament 32. The filament 32 is thereby heated and generates thermions. The filament 32 and the trap electrode 33 are respectively supplied with direct voltages having a predetermined potential difference. This potential difference accelerates the thermions generated from the filament 32 and makes them move to the trap electrode 33. Thus, a flow of thermions which move in the negative direction of the Y axis in their entirety is formed within the ionization chamber 30 (see the dashed arrows in FIG. 6). The sample component (compound) in the sample gas supplied through the sample-gas introduction tube 304 into the ionization chamber 30 comes in contact with the thermions and is thereby ionized. The magnets 34 and 35 create a magnetic field whose lines of magnetic induction are directed parallel to the Y axis. This magnetic field has the effect of preventing the flow of thermions from spreading in the X-axis direction as well as in the Z-axis direction.

The repeller electrode 31 is supplied with a direct voltage having the same polarity as the ions of sample origin, with its absolute value adjusted to be slightly larger than the potential of the ionization chamber 30 (in the present example, 0 V). By this voltage, an electric field for expelling the ions from the repeller electrode 31 toward the ion ejection opening 301 is created between the repeller electrode 31 and the ion ejection opening 301 in the ionization chamber 30. This expelling electric field causes the ions generated in a central area within the ionization chamber 30 to move toward the ion ejection opening 301. Meanwhile, the extraction electrode 36 is supplied with a direct voltage having an opposite polarity to the ions. The electric field created by this voltage penetrates into the ionization chamber 30 through the ion ejection opening 301. By the effects of the expelling and extracting electric fields combined together, the ions are extracted in the Z-axis direction from the ionization chamber 30 through the ion ejection opening 301 (see the thick arrow in FIG. 6), to be subjected to mass spectrometry.

CITATION LIST

Patent Literature
  Patent Literature 1: JP 2016-157523 A

SUMMARY OF INVENTION

Technical Problem

In the ion source 3, a contamination layer is formed on the inner wall surface of the ionization chamber 30 due to the adhesion of various substances, such as the compound molecules contained in the sample gas or ions originating from those molecules. If the contamination develops to a considerable extent, electrons will be adhered to the surface of the contamination layer, causing the electrostatic charging of the layer ("charge-up"). If the electric field within the ionization chamber 30 is significantly disturbed by the charge-up, the ions generated within the ionization chamber 30 will be more easily attracted toward the inner wall surface of the ionization chamber 30 and be eliminated due to the collision with the wall. This leads to a decrease in the amount of ions to be transported to the mass separator in the subsequent stage, and may consequently cause a decrease in analysis sensitivity or similar problem that prevents an accurate analysis. Therefore, as a routine operation, the user should perform maintenance work by deenergizing the device as well as removing and cleaning the ionization chamber (or other related units) when it seems that the inner wall surface of the ionization chamber (or related units) has been contaminated to such an extent that the charge-up will cause serious problems.

The aforementioned maintenance work is considerably cumbersome for the user since it must be performed every time a charge-up seems to have occurred. Furthermore, the aforementioned maintenance work requires not only time for dismantling and cleaning the device, but also time for starting the device to re-establish the vacuum state within the vacuum chamber. Therefore, the device will be unavailable for measurements for a certain period of time, so that the operation rate of the device will be lower. Allowing the charge-up to develop to a considerable extent during an analysis also causes the problem that the analysis result will be unreliable, so that the entire analysis will be useless.

The present invention has been developed to solve those problems. Its objective is to provide a method for mass spectrometry and a mass spectrometer capable of removing or reducing a charge-up which has occurred in an ion source, without requiring the device to be deenergized.

Solution to Problem

One mode of the present invention developed for solving the previously described problems is a method for mass spectrometry using a mass spectrometer including an ion source configured to ionize a component contained in a sample gas, the ion source including an ionization chamber having an ion ejection opening and internally having a space substantially separated from an outside area, a repeller electrode, located within the ionization chamber, for creating an expelling electric field which acts on an ion generated within the ionization chamber to expel the ion through the ion ejection opening to the outside area, and a voltage generator configured to apply a predetermined voltage to the repeller electrode, the method comprising:

a first step for creating the expelling electric field by applying a first voltage from the voltage generator to the repeller electrode; and a second step for creating an electric field for removing a charge-up by applying a second voltage from the voltage generator to the repeller electrode, where the second voltage is a positive voltage having a larger absolute value than the first voltage.

One mode of the present invention developed for solving the previously described problems is a mass spectrometer including an ion source configured to ionize a component contained in a sample gas, the ion source including:

an ionization chamber having an ion ejection opening and internally having a space substantially separated from an outside area;

a repeller electrode, located within the ionization chamber, for creating an expelling electric field which acts on an ion generated within the ionization chamber to expel the ion through the ion ejection opening to the outside area; and a voltage generator configured to selectively apply, to the repeller electrode, a first voltage for creating the expelling electric field and a second voltage for creating an electric field for removing a charge-up, where the second voltage is a positive voltage having a larger absolute value than the first voltage.

The ion source is an ion source which uses thermions for ionization. Specifically, it may be an ion source employing an EI, CI or NCI method.

Advantageous Effects of Invention

In the previously described mode of the method for mass spectrometry and the mass spectrometer according to the present invention, when a high positive voltage (i.e., the second voltage) is applied to the repeller electrode, a strong electric field in which electrons are forced to move toward the repeller electrode is created between the repeller electrode and the inner wall surface of the ionization chamber. Consequently, the electrons causing a charge-up are detached from the surface of the contamination layer formed on the inner wall surface of the ionization chamber, to ultimately come in contact with the repeller electrode and be eliminated.

Thus, the previously described mode of the method for mass spectrometry and the mass spectrometer according to the present invention can remove or reduce a charge-up which has occurred in the ionization chamber, without requiring the device to be deenergized or the vacuum state of the device to be cancelled. Accordingly, the user can decrease the frequency of the cumbersome maintenance work conventionally performed when a charge-up has occurred in the ion source, including the steps of deenergizing and dismantling the device as well as cleaning the ionization chamber (or the like). The burden of the user can be significantly reduced. The period of time in which the device is unavailable due to the maintenance work can also be shortened, so that the operation rate of the device will be improved. Additionally, since the operation for removing or reducing a charge-up can be performed in the middle of the analysis, a problem which will result if a charge-up occurs in the middle of the analysis can be avoided.

BRIEF DESCRIPTION OF DRAWINGS

FIGS. 2A and 2B are model diagrams showing the state of electrons within the ion source in the mass spectrometer according to the present embodiment, where FIG. 2A shows the situation in which a voltage of +1 V is applied to the repeller electrode, while FIG. 2B shows the situation in which a voltage of +100 V is applied to the repeller electrode.

DESCRIPTION OF EMBODIMENTS

A method for mass spectrometry and a mass spectrometer as one embodiment of the present invention is hereinafter described with reference to the attached drawings.

Figure 1:
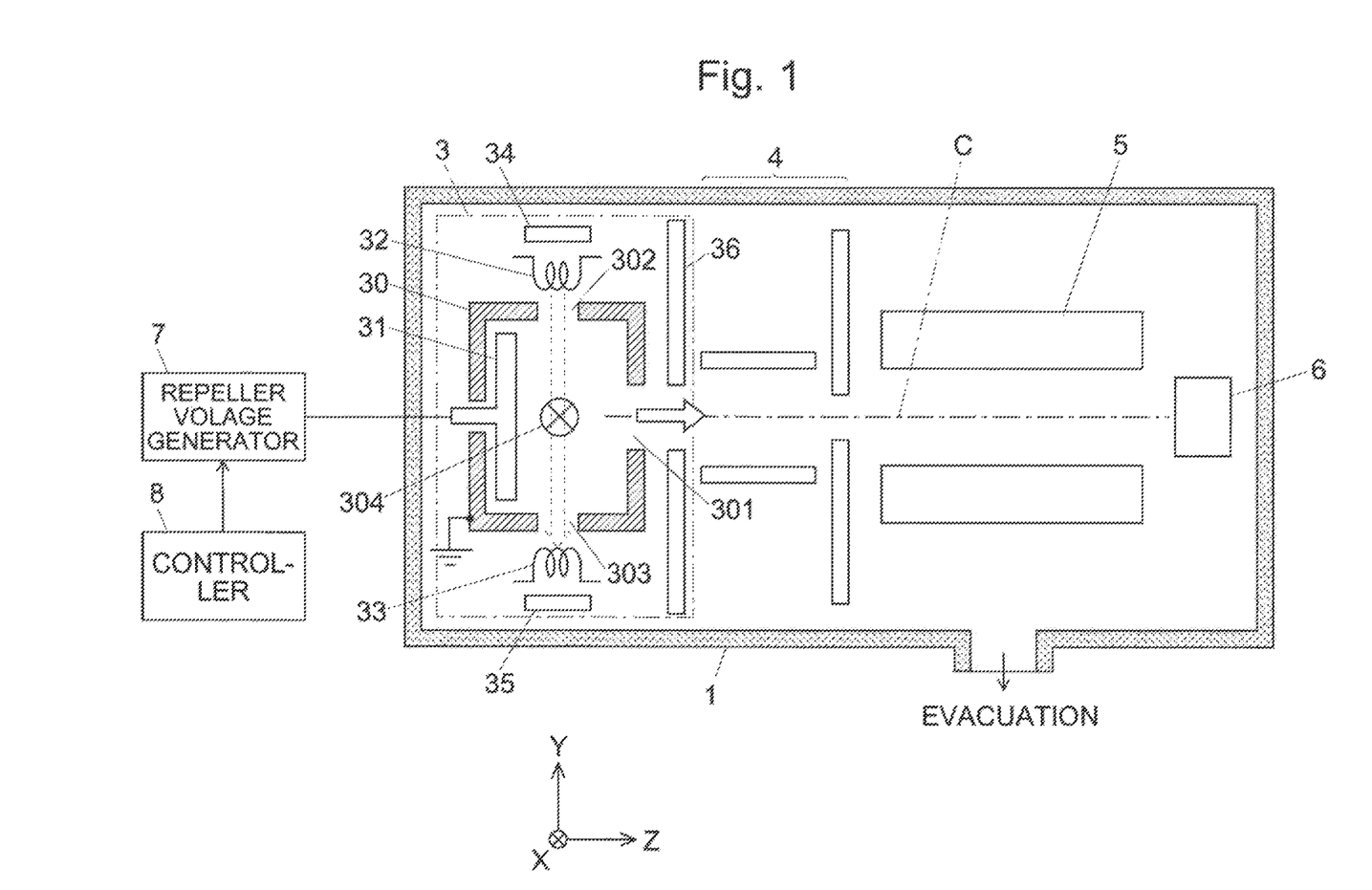
FIG. 1 is a configuration diagram of the main components of a mass spectrometer as one embodiment of the present invention.

FIG. 1 is a configuration diagram of the main components of the mass spectrometer according to the present embodiment. This mass spectrometer is a single quadrupole mass spectrometer.

As shown in FIG. 1, the mass spectrometer according to the present embodiment has a chamber 1 evacuated by a vacuum pump (not shown), within which an EI ion source 3, ion-transport optical system 4, quadrupole mass filter 5 as the mass separator, and ion detector 6 are arranged along an ion beam axis C.

The EI ion source 3 has the same structure as the one shown in FIG. 6. That is to say, the EI ion source 3 includes: an ionization chamber 30 having a substantially rectangular-parallelepiped outer shape and made of a metal or similar conductive material; a repeller electrode 31 located within the ionization chamber 30; a filament 32 located on the outside of an electron introduction opening 302 formed in the upper wall of the ionization chamber 30; a trap electrode 33 located on the outside of an electron discharge opening 303 formed in the lower wall of the ionization chamber 30; a pair of magnets 34 and 35 arranged so as to face each other, with the filament 32 and the trap electrode 33 in between; and an extraction electrode 36 located on the outside of the ion ejection opening 301. Additionally, a sample-gas introduction tube 304 is connected to a side wall of the ionization chamber 30.

The ionization chamber 30 is grounded and has a potential of 0 V. Under the control of a controller 8, a repeller voltage generator 7 applies a predetermined voltage to the repeller electrode 31. Though not shown in FIG. 1, the present mass spectrometer includes a voltage generator configured to apply predetermined voltages to the filament 32, trap electrode 33, extraction electrode 36 and other elements in the EI ion source 3, respectively. As a matter of course, the present device additionally includes a voltage generator configured to apply predetermined voltages to the ion transport optical system 4, quadrupole mass filter 5 and other sections in the subsequent stages, respectively.

Figure 2A:
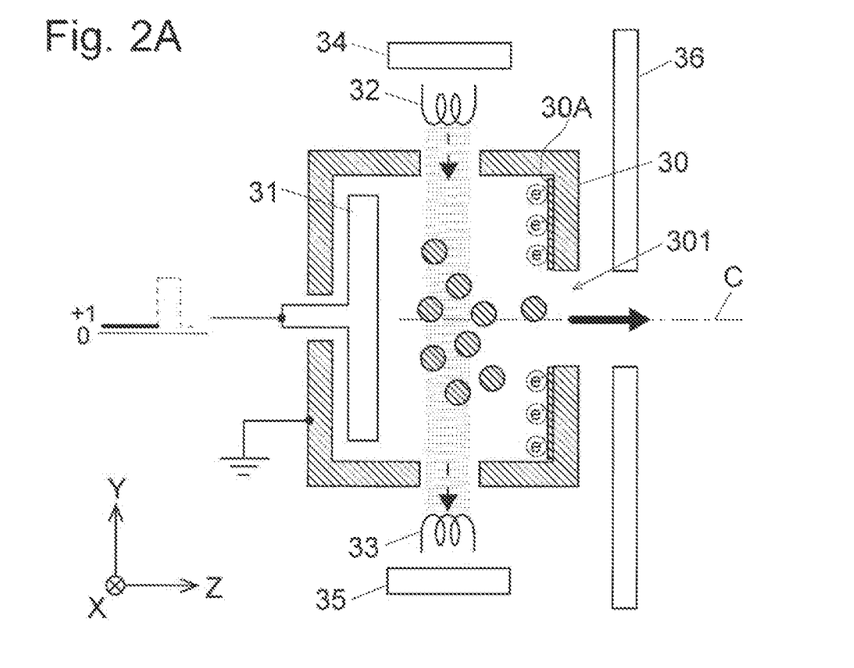
Figure 2B:
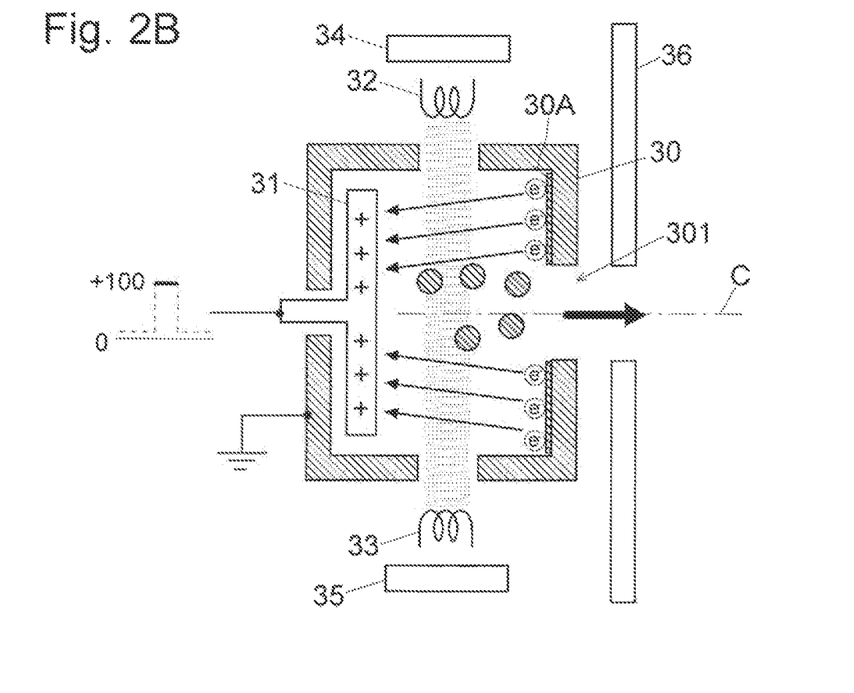
Figure 3:
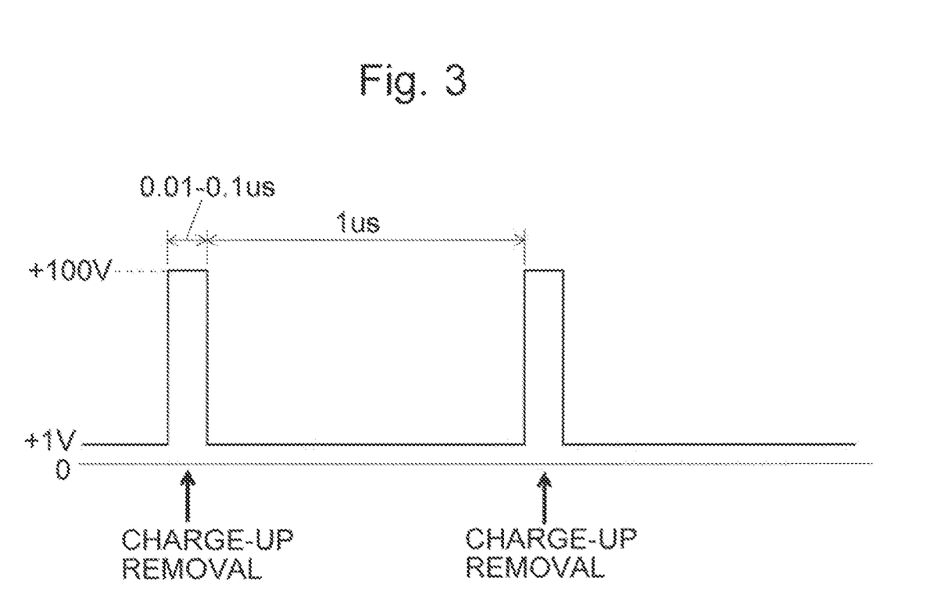
FIG. 3 is a diagram showing one example of the voltage waveform applied to the repeller electrode in the mass spectrometer according to the present embodiment.

Next, an operation for a mass spectrometric analysis performed in the mass spectrometer according to the present embodiment is described with reference to FIGS. 2A, 2B and 3. FIGS. 2A and 2B are model diagrams showing the state of electrons within the ion source 30. FIG. 3 is a diagram showing one example of the voltage waveform applied to the repeller electrode 31.

For example, a sample gas containing a plurality of compounds temporally separated from each other in a column of a gas chromatograph (not shown) is introduced into the ionization chamber 30 through the sample-gas introduction tube 304. An electric current is supplied to the filament 32. The filament 32 is thereby heated and generates thermions. Different voltages are applied to the filament 32 and the trap electrode 33, respectively, to create a potential difference between them. This potential difference imparts the thermions a certain amount of kinetic energy, so that the thermions leave the filament 32 and travel toward the trap electrode 33. Thus, a flow of thermions is formed from the filament 32 toward the trap electrode 33. The thermions fly within the magnetic field formed by the magnets 34 and 35, spiraling around the line of magnetic induction. Thus, the flow of thermions is prevented from spreading in the X-axis direction as well as in the Z-axis direction.

Under the control of the controller 8, the repeller voltage generator 7 applies, to the repeller electrode 31, a pulsed voltage having a low-level voltage value of +1 V and a high-level voltage value of +100 V, as shown in FIG. 3. The low-level voltage value is equal to the value of the voltage applied to the repeller electrode 31 for creating the expelling electric field within the ionization chamber 30 as in the conventional mass spectrometer. The pulse interval of the pulsed voltage applied to the repeller electrode 31 is equal to or greater than 10 times the pulse duration. For example, the interval of the neighboring pulses is 1 μsec, while the pulse duration is within a range from 0.01 to 0.1 μsec.

Within the ionization chamber 30, the compound molecules in the sample gas come in contact with the thermions and are thereby ionized. As shown in FIG. 2A, when the voltage applied to the repeller electrode 31 is +1 V, the expelling electric field created within the ionization chamber 30 by the potential difference between the repeller electrode 31 and the inner wall surface of the ionization chamber 30 (in the present case, 1 V) has the effect of expelling the ions (positive ions) generated in the previously described manner, whereby the ions are made to move roughly in the Z-axis direction, i.e., toward the ion ejection opening 301. Meanwhile, the extraction electrode 36 is supplied with a direct voltage having an opposite polarity to the ions. The extracting electric field created by this voltage penetrates into the ionization chamber 30 through the ion ejection opening 301. This extracting electric field has the effect of forcing the ions to move toward the ion ejection opening 301. By the effects of the expelling and extracting electric fields combined together, the ions generated by coming in contact with the thermions within the ionization chamber 30 are extracted through the ion ejection opening 301 to the outside area and introduced into the ion transport optical system 4.

Within the ion transport optical system 4, the ions are temporarily converged into an area near the ion optical axis C and sent to the quadrupole mass filter 5. The four rod electrodes forming the quadrupole mass filter 5 are supplied with a predetermined voltage consisting of a radiofrequency (RF) voltage added to a direct voltage. Only an ion having a specific mass-to-charge ratio corresponding to that voltage is selectively allowed to pass through the quadrupole mass filter 5. The ion detector 6 produces a detection signal corresponding to the amount of ions which have reached the same detector. Accordingly, for example, by controlling the applied voltage so that the mass-to-charge ratio of the ion which is allowed to pass through the quadrupole mass filter 5 continuously varies within a predetermined range, a set of mass spectrum data which show the ion intensity over the predetermined range of mass-to-charge ratios can be acquired.

A portion of the compound molecules contained in the sample gas and the generated ions collide with and adhered to the inner wall surface of the ionization chamber 30, forming a contamination layer 30A. FIG. 2A shows only the contamination layer 30A formed on the front wall of the ionization chamber 30 in which the ion ejection opening 301 is formed. Actually, the contamination layer will be formed on any area of the inner wall surface of the ionization chamber 30 to a greater or lesser extent. Since the contamination layer 30A is an electrically insulating layer, adhesion of thermions or other electrons to the surface of the contamination layer 30A causes a charge-up. This charge-up constitutes a major cause of the disturbance of the electric field created within the ionization chamber 30. In the present device, this charge-up is removed as follows when the voltage of +100 V is applied to the repeller electrode 31.

As shown in FIG. 2B, when the voltage applied to the repeller electrode 31 is switched to +100 V, the potential difference between the repeller electrode 31 and the inner wall of the ionization chamber 30 becomes dramatically larger than the previous value (potential difference: 1 V). Therefore, the electrons adhered to the contamination layer 30A on the inner wall surface of the ionization chamber 30 are detached by the strong positive electric field ("charge-up-removing electric field") and travel toward the repeller electrode 31, to ultimately come in contact with the repeller electrode 31 and be eliminated. Thus, the charge-up is removed, or at least significantly reduced if not completely removed.

The strong charge-up-removing electric field also affects the thermions. Therefore, a portion of the thermions which have entered the ionization chamber 30 through the electron introduction opening 302 are forced to deviate from the intended paths and be ultimately absorbed by the repeller electrode 31. However, since the thermions are given a large amount of acceleration energy, all thermions will not be eliminated, at least a portion of the thermions will contribute to the ionization of the sample components within the ionization chamber 30. Therefore, the ionization continues even during the period of time in which the voltage of +100 V is applied to the repeller electrode 31, although the ionization efficiency decreases. The charge-up-removing electric field also affects the behavior of the generated ions. However, the ions have far larger masses than the electrons and move much slower than the electrons. Accordingly, by setting a sufficiently short period of time for the application of the voltage of +100 V to the repeller electrode 31, it is possible to practically avoid an influence on the ejection of the ions from the ionization chamber 30 while applying the voltage during an analysis.

In the previously described example, the voltage of +100 V is applied to the repeller electrode 31 in order to remove the charge-up. A voltage of tens to hundreds of volts is preferable for detaching electrons adhered to the contamination layer 30A. Furthermore, as noted earlier, the duration of the high-voltage pulse should be as short as possible so as to minimize the influence on the ionization process or behavior of the ions. On the other hand, if the pulse duration is too short, the electrons detached from the contamination layer 30A cannot reach the repeller electrode 31, and the charge-up cannot be sufficiently removed. The minimally required duration of the pulse depends on the voltage value of the same pulse; the higher the voltage is, the shorter the pulse duration can be. The optimum duration of the pulse also depends on the distance between the repeller electrode 31 and the inner wall surface of the ionization chamber 30. Accordingly, an appropriate duration and voltage value of the pulse should be determined by experiments, simulations or similar methods. The same also applies to the pulse interval. Although the pulse interval in the previously described example is 1 μsec, it can be appropriately varied so as to reduce the influence on the ionization process or behavior of the ions.

Figure 4A:
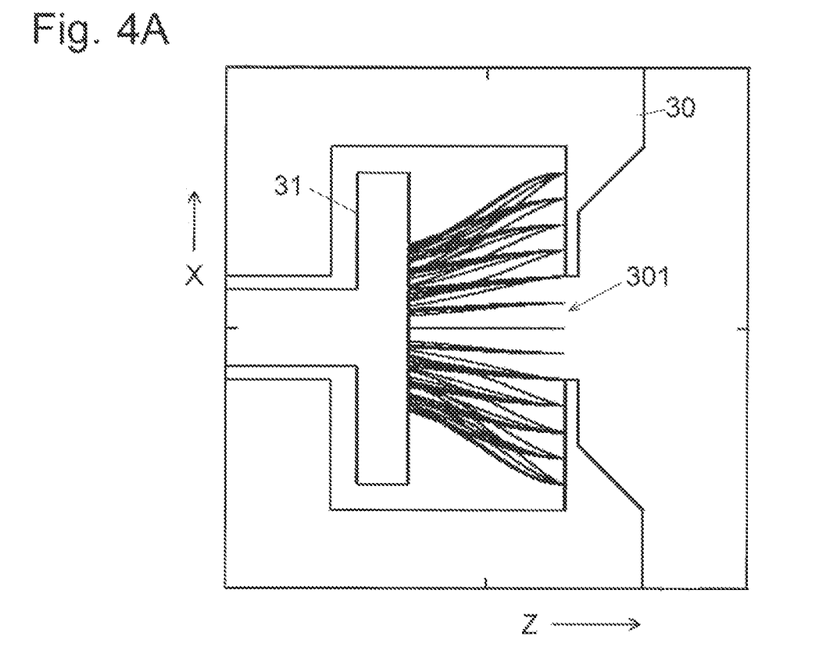
FIGS. 4A and 4B are diagrams showing the result of a simulation of the trajectories of electrons within an ionization chamber (when a thermion-converging magnetic field is not present).
Figure 4B:
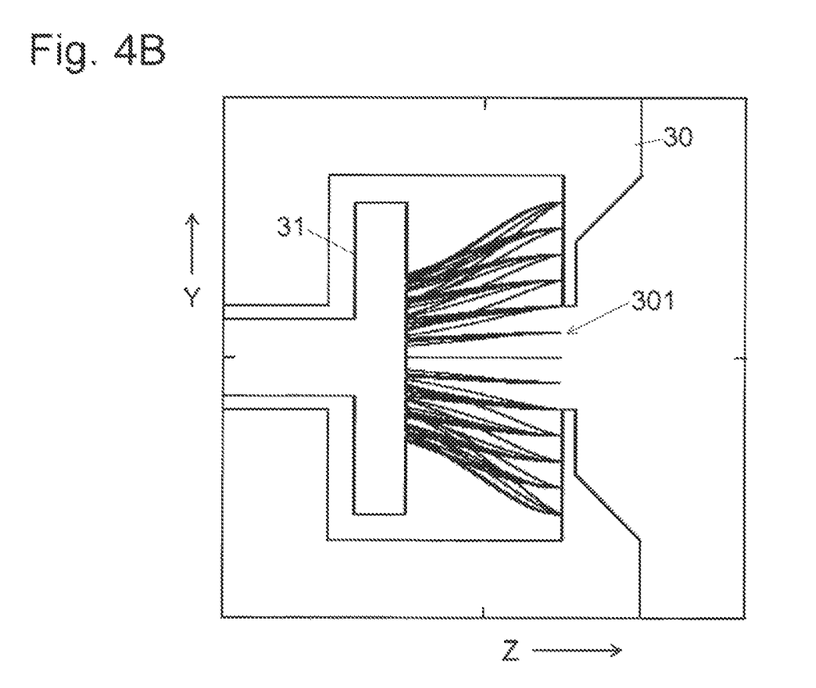
Figure 5A:
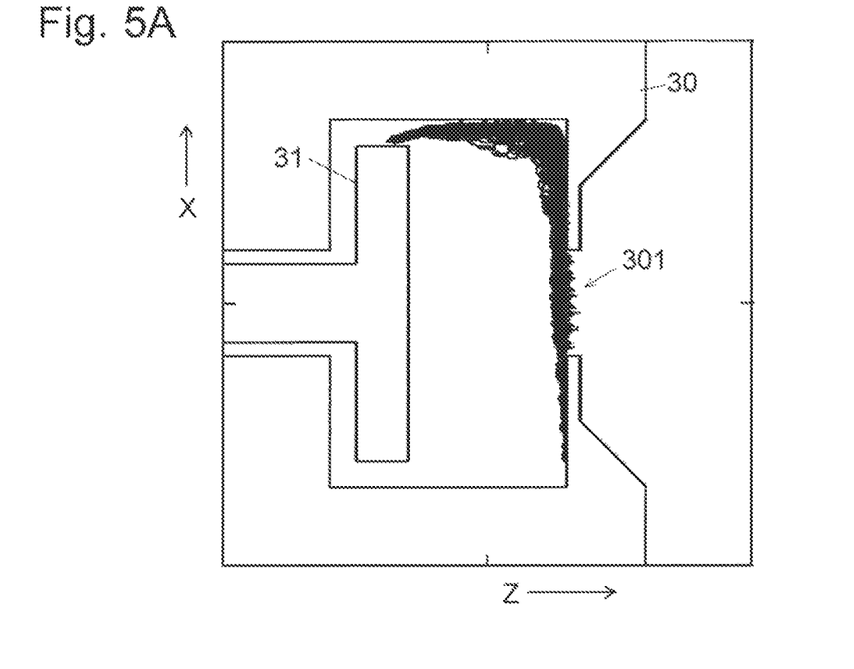
FIGS. 5A and 5B are diagrams showing the result of a simulation of the trajectories of electrons within an ionization chamber (when a thermion-converging magnetic field is present).
Figure 5B:
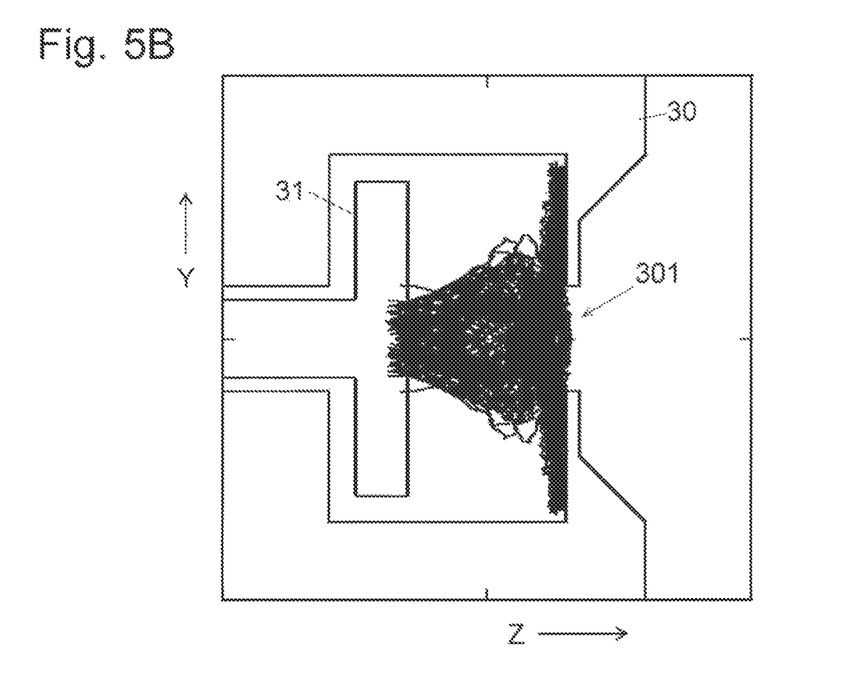

FIGS. 4A, 4B, 5A and 5B show the results of simulations of the trajectories of electrons within the ionization chamber 30. More specifically, FIGS. 4A and 4B illustrate the case where the thermion-converging magnetic field created by the magnets 34 and 35 is not present, while FIGS. 5A and 5B illustrate the case where the thermion-converging magnetic field created by the magnets 34 and 35 is present.

As shown in FIGS. 4A and 4B, when the thermion-converging magnetic field is not present, the electrons detached from the contamination layer on the inner surface of the front wall of the ionization chamber 30 almost directly travel toward the repeller electrode 31. On the other hand, as shown in FIGS. 5A and 5B, when the thermion-converging magnetic field created by the magnets 34 and 35 is present, the Lorentz force due to the magnetic field acts not only on the flow of thermions but also on the electrons detached from the contamination layer on the inner surface of the front wall of the ionization chamber 30. Therefore, the electrons show complicated motions, avoiding the area of the strong magnetic field and coming around toward the repeller electrode 31. In any of these cases, the electrons detached from the contamination layer 30A will ultimately reach the repeller electrode 31 and be eliminated by coming in contact with the repeller electrode 31.

As described to this point, the mass spectrometer according to the present embodiment periodically applies a high positive voltage to the repeller electrode 31 during an analysis in order to remove the charge-up. Therefore, the device can avoid the situation in which the amount of ions to be subjected to the analysis is decreased due to an occurrence of a charge-up in the ion source 3 in the middle of the analysis. Consequently, a high level of analysis sensitivity can be ensured. Since the charge-up can be sufficiently suppressed until the contamination layer grows to a certain extent, the frequency of the maintenance work for removing the contamination layer can be decreased.

The mass spectrometer according to the previously described embodiment may additionally be configured to perform a charge-up-removing operation by applying, to the repeller electrode 31, a voltage of +100 V or an appropriate voltage of tens to hundreds of volts for a predetermined period of time at various timings as needed, e.g., at an appropriate timing according to a user operation, in addition to the charge-up-removing operation which is repeatedly performed during the analysis under the control of the controller 8. This configuration enables an appropriate voltage for removing the charge-up (e.g. the voltage of +100 V) to be applied to the repeller electrode 31 upon a predetermined user operation, whether or not during the analysis. In this configuration, the user operation may be acceptable only outside the analysis period.

An appropriate voltage for removing the charge-up may be applied to the repeller electrode 31 at an appropriate timing predetermined outside the analysis period under the control of the controller 8. For example, an appropriate charge-up-removing voltage can be automatically applied to the repeller electrode 31 after each specified mass spectrometry (e.g. GC-MS on one sample) for a predetermined period of time or immediately before such mass spectrometry.

The descriptions thus far have been concerned with the case of generating positive ions in the ion source 3. It is evident that, in the case of generating negative ions, a negative voltage (e.g., −1 V) should be applied to the repeller electrode 31 during the period in which the expelling electric field should be created, while a high positive voltage (e.g., +100 V) can be applied to the repeller electrode 31 during the period in which the charge-up-removing electric field should be created.

Although the ion source in the mass spectrometer according to the previously described embodiment is an EI ion source, the present invention can also be applied to any type of mass spectrometer including an ion source which ionizes the components of sample origin within an ionization chamber and ejects the generated ions from the ionization chamber by means of a repeller electrode. Specific examples include mass spectrometers having a CI ion source or NCI ion source.

It should be noted that the previously described embodiment is a mere example of the present invention. Any modification, change or addition appropriately made within the spirit of the present invention will evidently fall within the scope of claims of the present application.

For example, the configuration of the device except for the ion source is not limited to that of the previously described embodiment and may be appropriately changed. Accordingly, as a matter of course, the present invention is not limited to a single quadrupole mass spectrometer but is applicable to various types of mass spectrometers, including time-of-flight mass spectrometers, ion trap mass spectrometers, tandem mass spectrometers and ion-mobility mass spectrometers.

Various Modes of Invention

A person skilled in the art can understand that the previously described illustrative embodiment is a specific example of the following modes of the present invention.

(Clause 1) One mode of the a method for mass spectrometry according to the present invention is a method for mass spectrometry using a mass spectrometer including an ion source configured to ionize a component contained in a sample gas, the ion source including an ionization chamber having an ion ejection opening and internally having a space substantially separated from an outside area, a repeller electrode, located within the ionization chamber, for creating an expelling electric field which acts on an ion generated within the ionization chamber to expel the ion through the ion ejection opening to the outside area, and a voltage generator configured to apply a predetermined, the method comprising:

a first step for creating the expelling electric field by applying a first voltage from the voltage generator to the repeller electrode; and a second step for creating an electric field for removing a charge-up, by applying a second voltage from the voltage generator to the repeller electrode, where the second voltage is a positive voltage having a larger absolute value than the first voltage.

(Clause 7) One mode of the mass spectrometer according to the present invention is a mass spectrometer including an ion source configured to ionize a component contained in a sample gas, the ion source including:

an ionization chamber having an ion ejection opening and internally having a space substantially separated from an outside area;

a repeller electrode, located within the ionization chamber, for creating an expelling electric field which acts on an ion generated within the ionization chamber to expel the ion through the ion ejection opening to the outside area; and a voltage generator configured to selectively apply, to the repeller electrode, a first voltage for creating the expelling electric field and a second voltage for creating an electric field for removing a charge-up, where the second voltage is a positive voltage having a larger absolute value than the first voltage.

Thus, the method for mass spectrometry described in Clause 1 and the mass spectrometer described in Clause 7 can remove or reduce a charge-up which has occurred in the ionization chamber, without requiring the device to be deenergized or the vacuum state of the device to be cancelled. Accordingly, the user can decrease the frequency of the cumbersome maintenance work conventionally performed when a charge-up has occurred in the ion source. The burden of the user can be significantly reduced. The period of time in which the device is unavailable due to the maintenance work can also be shortened, so that the operation rate of the device will be improved. Additionally, since the operation for removing or reducing a charge-up can be performed in the middle of the analysis, a problem which will result if a charge-up occurs in the middle of the analysis can be avoided.

(Clause 2) In the method for mass spectrometry described in Clause 1, the voltage generator may apply, to the repeller electrode, a pulsed voltage in which the low level is equal to the first voltage and the high level is equal to the second voltage.

The method for mass spectrometry described in Clause 2 can perform the ionization within the ionization chamber mainly during the low-level period of the pulsed voltage, while carrying out the charge-up-removing operation during the high-level period of the pulsed voltage. This configuration enables the device to continuously perform an analysis while avoiding an occurrence of the charge-up within the ion source.

(Clause 3) In the method for mass spectrometry described in Clause 2, the duration of the pulse whose voltage value is equal to the second voltage may be determined according to the period of time required for electrons causing a charge-up on the inner wall surface of the ionization chamber to be attracted to and reach the repeller electrode due to the electric field for removing a charge-up.

The method for mass spectrometry described in Clause 3 can assuredly remove or reduce the charge-up during the high-level period of the pulsed voltage. Furthermore, the period for the charge-up-removing operation can be prevented from being unnecessarily long, and its influence on the ion-generating operation within the ion source can be minimized.

(Clause 4) In the method for mass spectrometry described in one of Clauses 1-3, the second step may be carried out in place of the first step during an analysis (Clause 5) In the method for mass spectrometry described in Clause 4, the second step may be repeatedly carried out in place of the first step during an analysis.

"During an analysis" in the method for mass spectrometry described in Clause 4 or 5 corresponds to a period in which ions of sample component origin to be subjected to mass spectrometry are generated within the ion source. The method for mass spectrometry described in Clause 4 or 5 makes it possible to avoid an occurrence of the charge-up within the ion source during the analysis. Accordingly, a problem such as a decrease in analysis sensitivity which will result if the charge-up develops to a considerable extent in the middle of the analysis can be prevented.

(Clause 6) In the method for mass spectrometry described in one of Clauses 1-3, the first step may be carried out during an analysis and the second step may be carried out in at least a portion of a period outside an analysis period.

The method for mass spectrometry described in Clause 6 can remove the charge-up within the ion source, without causing an influence on the analysis result with respect to sensitivity or accuracy. Outside the analysis period, applying the charge-up-removing voltage to the repeller electrode can be continued for a longer period of time than during the analysis. Accordingly, the charge-up can be more assuredly removed.

REFERENCE SIGNS LIST

1 . . . Chamber
3 . . . Ion Source
30 . . . Ionization Chamber
301 . . . Ion Ejection Opening
302 . . . Electron Introduction Opening
303 . . . Electron Discharge Opening
304 . . . Sample-Gas Introduction Tube
30A . . . Contamination Layer
31 . . . Repeller Electrode
32 . . . Filament
33 . . . Trap Electrode
34, 35 . . . Magnet
36 . . . Extraction Electrode
4 . . . Ion Transport Optical System
5 . . . Quadrupole Mass Filter
6 . . . Ion Detector
7 . . . Repeller Voltage Generator
8 . . . Controller
C . . . Ion Beam Axis

The invention claimed is:

1. A method for mass spectrometry using a mass spectrometer including an ion source configured to ionize a component contained in a sample gas, the ion source including an ionization chamber having an ion ejection opening and internally having a space substantially separated from an outside area, a repeller electrode, located within the ionization chamber, for creating an expelling electric field which acts on an ion generated within the ionization chamber to expel the ion through the ion ejection opening to the outside area, and a voltage generator configured to apply a predetermined voltage to the repeller electrode, the method comprising:
- a first step for creating the expelling electric field by applying a first voltage from the voltage generator to the repeller electrode; and
- a second step for creating an electric field for removing a charge-up, by applying a second voltage from the voltage generator to the repeller electrode, where the second voltage is a positive voltage having a larger absolute value than the first voltage.

2. The method for mass spectrometry according to claim 1, wherein the voltage generator applies, to the repeller electrode, a pulsed voltage in which the low level is equal to the first voltage and the high level is equal to the second voltage.

3. The method for mass spectrometry according to claim 2, wherein a duration of a pulse whose voltage value is equal to the second voltage is determined according to a period of time required for electrons causing a charge-up on an inner wall surface of the ionization chamber to be attracted to and reach the repeller electrode due to the electric field for removing a charge-up.

4. The method for mass spectrometry according to claim 1, wherein the second step is carried out in place of the first step during an analysis.

5. The method for mass spectrometry according to claim 4, wherein the second step is repeatedly carried out in place of the first step during an analysis.

6. The method for mass spectrometry according to claim 1, wherein the first step is carried out during an analysis and the second step is carried out in at least a portion of a period outside an analysis period.

7. A mass spectrometer including an ion source configured to ionize a component contained in a sample gas, wherein the ion source includes:
- an ionization chamber having an ion ejection opening and internally having a space substantially separated from an outside area;
- a repeller electrode, located within the ionization chamber, for creating an expelling electric field which acts on an ion generated within the ionization chamber to expel the ion through the ion ejection opening to the outside area; and
- a voltage generator configured to selectively apply, to the repeller electrode, a first voltage for creating the expelling electric field and a second voltage for creating an electric field for removing a charge-up, where the second voltage is a positive voltage having a larger absolute value than the first voltage.

* * * * *